United States Patent [19]
Kelm

[11] Patent Number: 6,103,769
[45] Date of Patent: Aug. 15, 2000

[54] PHARMACEUTICAL COMPOSITION CONTAINING NITRIC OXIDE

[75] Inventor: Malte Kelm, Düsseldorf, Germany

[73] Assignee: Schwarz Pharma AG, Monheim, Germany

[21] Appl. No.: 09/125,085

[22] PCT Filed: Feb. 3, 1997

[86] PCT No.: PCT/EP97/00482

§ 371 Date: Jul. 30, 1998

§ 102(e) Date: Jul. 30, 1998

[87] PCT Pub. No.: WO97/28810

PCT Pub. Date: Aug. 14, 1997

[30] Foreign Application Priority Data

Feb. 7, 1996 [DE] Germany .......................... 196 04 361

[51] Int. Cl.[7] .................................................. A61K 33/00
[52] U.S. Cl. .......................... 514/769; 514/824; 514/929; 514/970; 428/718; 604/24; 604/507; 604/508; 604/509
[58] Field of Search ............................ 424/718; 514/769, 514/824, 929, 970; 604/24, 507, 508, 509

[56] References Cited

U.S. PATENT DOCUMENTS 5,536,241  7/1996  Zapol ......................................... 604/23

FOREIGN PATENT DOCUMENTS 9400180  6/1994  WIPO .
9526725  12/1995  WIPO .

OTHER PUBLICATIONS

European Journal of Gastroenterology & Hepatology, 1995, vol. 7 No. 3, David C. Rees, et al., Are serum concentrations of nitric oxide metabolites useful for predicting the clinical outcome of severe ulcerative colitis?, p. 227–230.

Spectrophotometric Detection of Nitrogen Oxides Using Azo Dyes, W. Ross Tracey, vol. 1, No. 2, Oct., pp. 125–131, 1992.

Research Advances Series, David G. Harrison, MD et al, The Nitrovasodilators New Ideas About Old Drugs, pp. 1461–1467 vol. 87, No. 5, May 1993.

Journal of Chromatography, Steven A. Everett, et al, Nitric oxide in biological fluids: analysis of nitrite by high–performance ion chromatography, pp. 437–442, 1993.

Journal of Cardiovascular Pharmacology 17 (Suppl.3) S25–S33—M. Feelisch, The Biochemical Pathways of Nitric Oxide Formation from Nitrovasodialtors: Appropriate Choice of Exogenous NO Donors and Aspects of Preparation and Handling of Aqueous NO Solutions, 1993.

Role of Nitric Oxide in the Regulation of Coronary Vascular Tone in Hearts from Hypertensive Rats, Malte Kelm et al—vol. 25, No. 2 Feb. 1995.

Abstract of Japanese Patent No. JP7165610 Jun. 27, 1995.

*Primary Examiner*—Frederick Krass
*Attorney, Agent, or Firm*—Fulbright & Jaworski, LLP

[57] ABSTRACT

Disclosed are pharmaceutical composition of a sterile, injectable physiologically acceptable solution containing nitric oxide (NO), processes for preparing the compositions and a process for detecting physiologically present NO. With these NO solutions, NO in high doses can trigger locally in vessels, e.g. coronary vessels, specific local biological effects such as relaxation of the smooth vascular musculature, inhibition of thee adhesion of thrombocytes, etc., without producing systemic side-effects, such as for example, a critical drop in blood pressure, in spite of the high does. The detection process enables the presence of an endothelial dysfunction to be established from the whole blood of humans and other mammals.

7 Claims, 7 Drawing Sheets

PHARMACEUTICAL COMPOSITION CONTAINING NITRIC OXIDE

DESCRIPTION

The present invention concerns a pharmaceutical composition of a sterile, injectable physiologically acceptable solution containing nitric oxide (NO), a method for its preparation and a detection method for physiologically present NO.

Physiologically present nitric oxide (NO), through a variety of biological functions, can influence essential key processes in the development of arteriosclerosis, such as relaxation of smooth vascular muscles, inhibition of adhesion of thrombocytes, granulocytes and monocytes to the vascular wall, inhibition of proliferation of secretory smooth muscle cells and direct effects on endothelial metabolism.

Thus, in recent years it has been shown that endothelial nitric oxide (NO) influences the metabolism as well as the function of the vascular wall by a great many mechanisms:

1. by stimulation of soluble guanylate cyclase it leads to the relaxation of smooth vascular muscles, and
    2. thus participates in the regulation of peripheral vascular resistance and arterial blood pressure,
    3. in addition, it inhibits mitogenesis and proliferation of smooth vascular muscle cells,
    4. it suppresses adhesion of thrombocytes, monocytes and neutrophil granulocytes to the vascular wall, and
    5. it directly influences the metabolism of endothelial cells, e.g., by altered expression of adhesive molecules on the superficial membrane. Overviews of this are found in:
       1. Moncada, S. and Higgs, A. The L-arginine-nitric oxide pathway. N.Engl.J.Med. 329: 2002–2012, 1993.
       2. Radomski, M. W. and Moncada, S. Regulation of vascular homeostasis by nitric oxide. Thromb. Haemost. 70:36–41, 1993
       3. Snyder, S. H. and Bredt, D. S. Biological roles of nitric oxide. Sci AM 266 (5):68–77, 1992.
       4. Gibbons, G. H. and Dzau, V. J. The emerging concept of vascular remodeling. N.Engl.J.Med. 330:1431–1438, 1994.

All of the processes mentioned represent key events in the development of pathologic vascular wall changes in arteriosclerosis. Recognized risk factors of arteriosclerosis, which also affect endothelial function, are arterial hypertension, hyperlipoproteinemia, diabetes mellitus, nicotine consumption and possibly age and sex (see Moncada, S. and Higgs, A. The L-arginine-nitric oxide pathway. N. Engl. J. Med. 329:2002–2012, 1993, Ross, R. The pathogenesis of atherosclerosis—an update. N. Engl. J. Med. 324 (No. 8):488–500, 1986; Safar, M. E. and Frohlich, E. D. The arterial system in hypertension. A prospective view. Hypertension 26:10–14, 1995).

However, the pathophysiologically significant demonstration of altered activity of endothelial NO synthesis has hitherto been successful only in experimental preparations with cultured cells or isolated organ circulatory systems in which a quantification of NO or its catabolic products was possible. Regarding this, however, in man so far only phenomenological findings with regard to an altered acetylcholine-induced flow response in various vascular regions have been described as indirect markers of endothelium-dependent vasodilatation. Exact quantification of the activity of endothelial constitutive NO synthesis in man as an indicator of endothelial dysfunction has previously not been possible.

Lastly, in past decades a variety of classes of NO donors for the treatment of arteriosclerotic vascular wall alterations such as, for example, coronary heart disease, have been successfully developed and employed (overviews on this are found in Feelisch, M. The biochemical pathways of nitric oxide formation from nitrovasodilators: appropriate choice of exogenous NO donors and aspects of preparation and handling of aqueous NO solutions. J. Cardiovasc. Pharmacol. 17 (suppl. 3): S25–S33, 1991; Feelisch, M. and Noack, E. The vitro metabolism of nitrovasodilators and their conversion into vasoactive species. In: Heart Failure Mechanism- and Management, edited by Lewis, B. S. and Kimchi, A., Springer: Berlin, Heidelberg, 1991, p. 241–255; Harrison, D. G. and Bates, J. N. The nitrovasodilators. Circulation 87:1461–1467, 1993; De Caterina, R. Nitrate als Thrombozytenfunctionshemmer [Nitrates as thrombocyte function inhibitors]. Z. Kardiol. 83:463–473, 1994).

NO donors act in the arterial as well as in the venous portion of the circulatory system and also influence NO-dependently the interaction of the vascular wall with the corpuscular components of the blood (thrombocytes, neutrophil granulocytes and monocytes). To date, however, there has as yet been no therapeutic development that permits NO to be used directly in the form of authentic NO solutions in the human circulatory system. This may have its roots in the extremely rapid metabolism and inactivation of NO in the human circulatory system which, on the one hand, impedes successful and targeted introduction of NO into the human circulatory system but, on the other, offers the advantage of potentially being able to obtain very high NO doses locally without having to put up with accompanying systemic side effects. With regard to the abovementioned extensive antiarteriosclerotic properties of NO, the last point in particular seems extremely significant for all intravascular interventions in peripheral and coronary arteries.

Over 370,000 coronary interventions (PTCA, etc.) annually are now performed in highly developed industrial nations such as the USA and Germany (see Gleichmann, U., Mannebach, H., and Lichtlen, P. 10. Bericht über Struktur und Lei ungszahlen der Herzkatheterlabors in der Bundesrepublik Deutschland [Report on structure and performance of the cardiac catheter laboratory in the Federal Republic of Germany]. Z. Kardiol. 84:327–333, 1995).

The initial rate of success runs to 90%, but 10% of PTCAs lead to early occlusion or thrombus formation. In addition, in 25–50% of cases, depending upon the reference cited, restenosis develops in the first six months after surgery. The total number of all angioplasties performed worldwide is estimated at over one million by the year 2000, which in turn means that up to 400,000 restenoses annually are to be expected. These figures underscore the urgent need for treatment to reduce the rate of acute and long-term restenosis after PTCA. Systemic pharmacologic studies of intervention with calcium antagonists, organic nitrates and ACE inhibitors have so far shown no effect on the rate of restenosis. Even the development of a variety of alternative mechanical methods (directional atherectomy, laser angioplasty, stent implantation, rotablation) has failed to result in an overall reduction of the rate of restenosis, these methods remaining limited to certain niche indications. This has recently led to the development of new LDD (local drug delivery) systems, such as coated stent prostheses, the Kaplan-Simpson infusion catheter (Stanford University), the microinfusion catheter (Cordis) or the porous PTCA balloon catheter (ACS). With these systems it seems possible for the first time to introduce high local doses of a medicinal drug into the vascular wall of the coronary arteries. Because of NO's rapid metabolism in human blood, it now seems extremely desirable and useful to introduce NO into the coronary vessel locally in high doses during coronary interventions and thus to utilize all the biological effects of NO mentioned by way of introduction, such as relaxation of smooth vascular muscles, inhibition of adhesion of thrombocytes and neutrophil monocytes, at a local spot without accompanying systemic effects, such as, for example, a critical pressure drop, developing because of high doses.

As already mentioned at the beginning, arterial hypertension, hyperlipoproteinemia and diabetes mellitus are the essential atheriogenic risk factors. Epidemiologic data indicate a total mortality rate of 25% for arterial hypertension and its secondary cardiovascular diseases alone; (see Strauer, B. E. Das Hochdruckherz [The hypertensive heart], Berlin, Heidelberg, New York: Springer Verlag, 1991, pp. 1–241).

Endothelial dysfunction, which may be defined as the essential pacemaker of arteriosclerosis, has to date not been detectable by any routine clinical parameter. Consequently, from the general point of view of an early diagnosis, as well as a differential therapeutic influence on such endothelial dysfunction, a reliable detection method for the field of cardiovascular medicine is desirable.

The object of the present invention therefore is to make available a pharmaceutical composition of a sterile, injectable physiologically acceptable solution having a NO content, a method for its preparation and a detection method for physiologically present NO.

This object has been accomplished as explained below and as disclosed in the claims.

According to an embodiment of the invention, the pharmaceutical composition consists of 0.9% physiological sodium chloride solution saturated with NO.

In the pharmaceutical composition according to the invention the saturation concentration of NO in the 0.9% sodium chloride solution decreases differentially with increasing temperature.

According to an especially advantageous embodiment of the invention, the values of the saturation concentration with NO of the 0.9% sodium chloride solution at 0° C. are 3.26 NO [$\mu$mol/L], at 25° C. 1.85 NO [$\mu$mol/L], at 37° C. 1.52 NO [$\mu$mol/L] and at 50° C. 1.26 NO [$\mu$mol/L].

According to the invention, the pharmaceutical composition is prepared in that, with the exclusion of oxygen, argon is passed through a sterile, injectable 0.9% sodium chloride solution until any residual oxygen content has been removed and then NO is passed through it up to the saturation concentration of NO in the 0.9% sodium chloride solution.

According to another embodiment of the invention, the NO solution according to the invention may be used for the preparation of a pharmaceutical composition for the treatment of endothelial dysfunction in mammals.

The following Example 1 explains the structure of the device for the preparation of a sterile, injectable NO solution and its preparation.

EXAMPLE 1 a) Configuration of Apparatus

Figure 1:
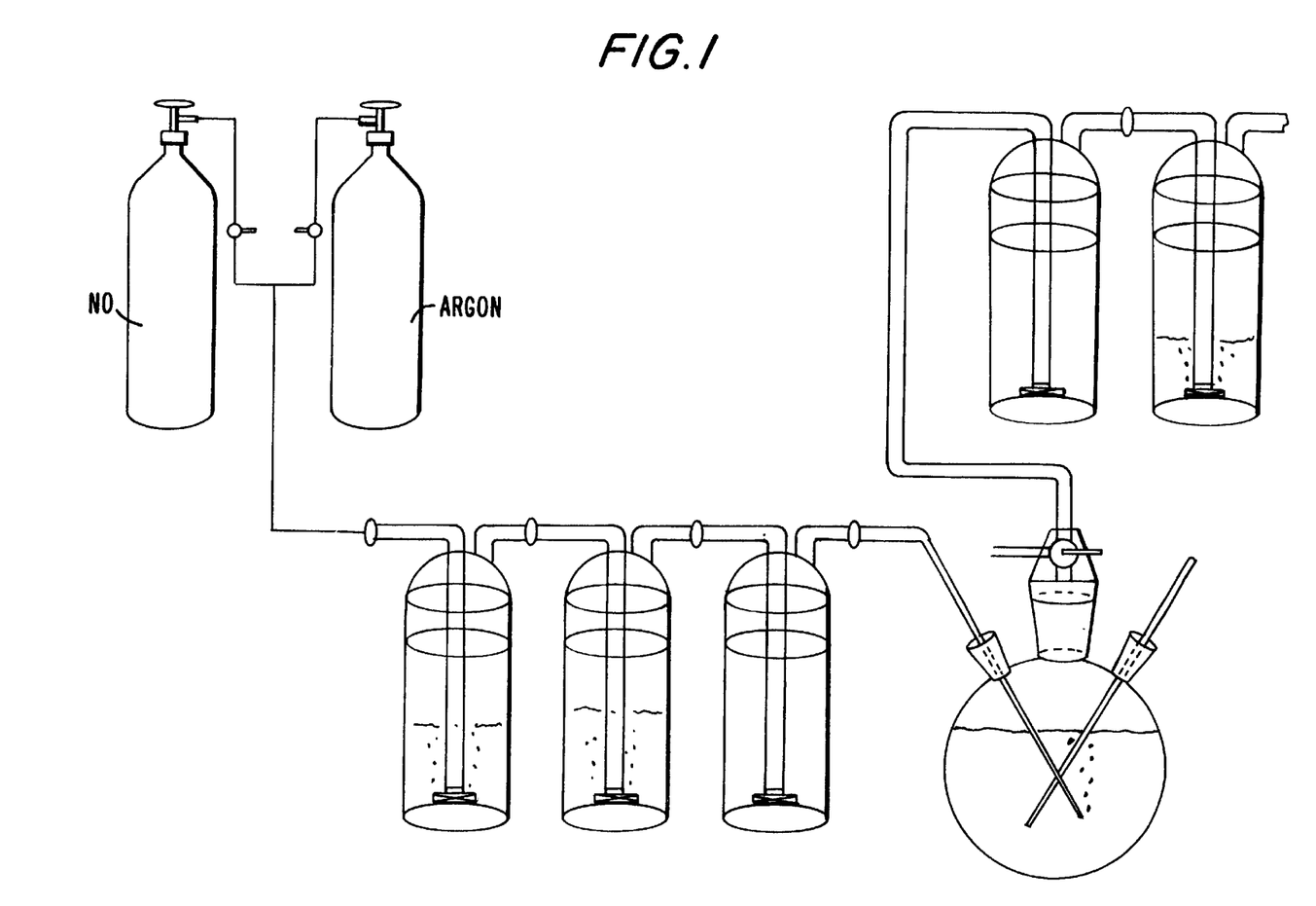
FIG. 1 depicts a system for the preparation of NO solutions.
Figure 2A:
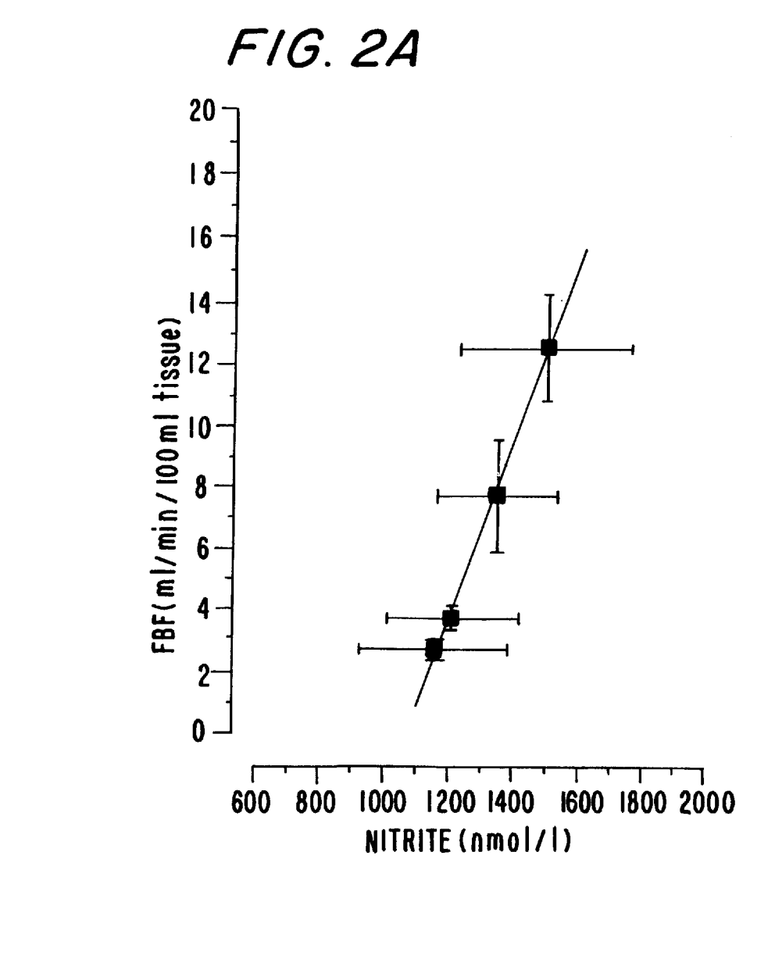
Figure 2B:
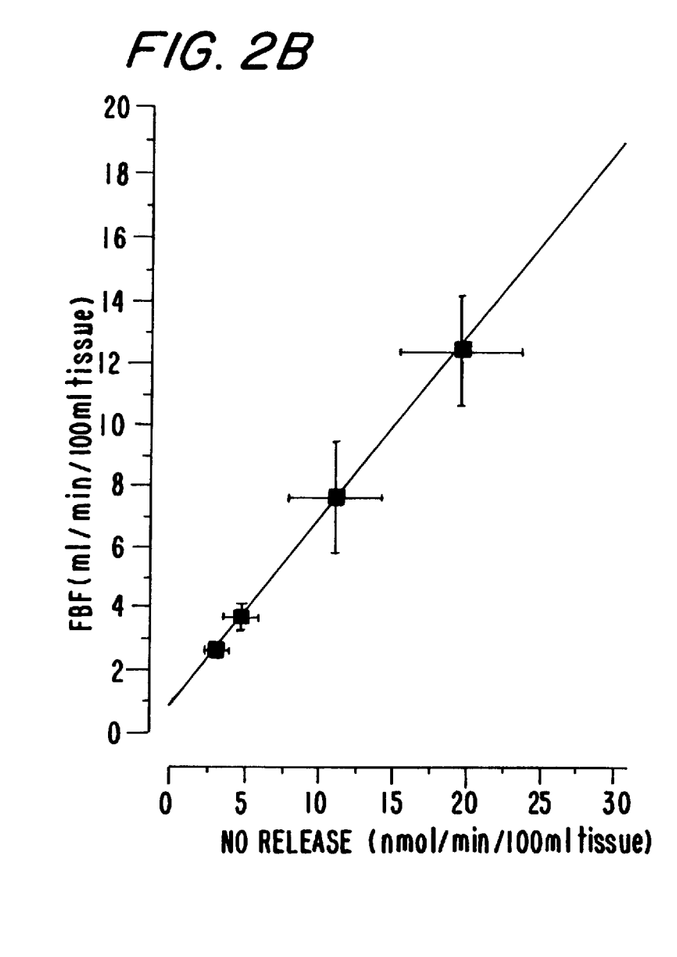
Figure 3A:
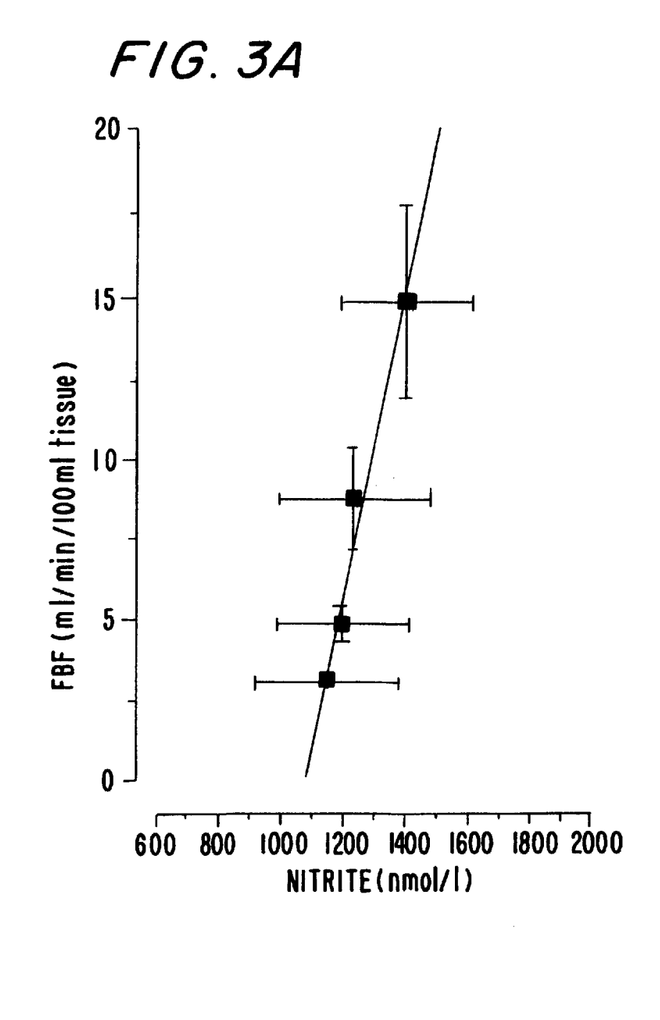
Figure 3B:
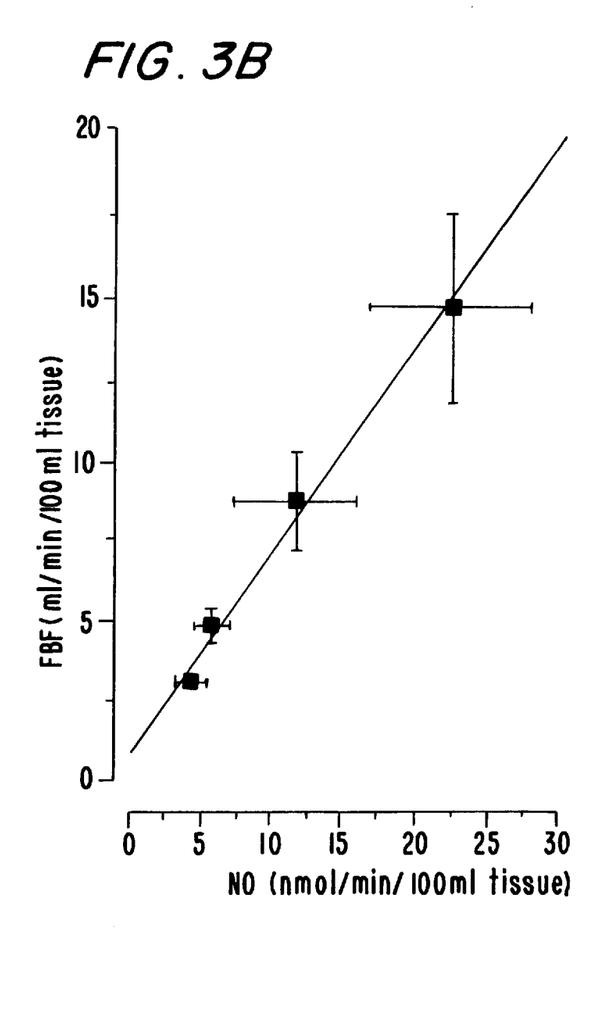

The configuration of the apparatus is shown in Drawing 1, wherein 1 denotes a NO 3.0 reservoir (AGA);

2, an argon 5.0 reservoir (Linde);

3, a gas washing bottle with 5% pyrogallol (pyrogallol z.A. 612, Merck) in saturated KOH (w:v);

4, a gas washing bottle with KOH z.A. 5033 (Merck), 20%;

5, a gas washing bottle, dry;

6, a round bottom three-necked flask (250 ml), charged with 0.9% NaCl solution with 3 ground inserts, in each of which there are incorporated:
   a) a stopcock
   b) a Luer-lock three-way stopcock
   c) a three-way stopcock 7, a gas washing bottle, empty, as water trap 8, a gas washing bottle with KOH z.A. 5033 (Merck), as water trap;

A denotes the respective gas-tight ground joints;

B, a gas-tight three-way stopcock;

C denotes gas-tight ground joints;

D, a gas-tight three-way cock;

E, gas-tight ground joints for connection of the respective gas washing bottles.

All parts of the apparatus are connected by gas-tight hoses (type Tygon R 3603). Teflon Plastibrand (Brand) seals are used as seals and, as filters, Millex type GS filters, 0.2 $\mu$m (millipore).

b) Preparation of a Sterile NO Solution

All glassware is cleaned by means of concentrated caustic soda solution (NaOH) and in every case rewashed 10 times with aqua bidestillata and HPLC water. Then the successively connected gas washing bottles (3), (4), (5), of which in (3) pyrogallol (5%) in saturated KOH (w:v) is placed for the removal of traces of oxygen, in (4) 20% KOH is placed for the removal of higher nitrogen oxides and (5) is dry, and the three-necked round bottom flask connected therewith, in which NaCl solution (0.9%) is placed, are gassed for 45 min with argon. The portion of the NaCl solution found in the riser tube is discarded. The oxygen is removed from a sterile, gas-tight syringe and the associated conducting systems as well as filters by a sterile 0.2 $\mu$m filter by means of argon and the volume of NaCl necessary for dilution of the NO solution is discharged into the oxygen-free, gas-tight syringe. Lastly, the system is gassed for 45 min with nitrogen oxide (NO).

Oxygen is completely removed anew with argon from the filters and conducting systems that lead to the syringe with dilution solution present. The portion of NO solution found within the riser tube is discarded and after that the entire conducting system and the sterile filter are thoroughly washed with NO solution. The necessary volume of NO solution is immediately transferred into the gas-tight primary packing previously prepared with given NaCl solution via the three-way stopcock (B) through sterile filters, which may in each instance be an ampoule, vial, syringe, etc.

An additional embodiment of the invention is a detection method for the quantitative determination of endothelial dysfunction in mammals.

Previously, endothelial dysfunction in patients with arterial hypertension, diabetes mellitus and/or hyperlipoproteinemia could only be established by costly diagnostic measures such as arterial puncture with subsequent local administration of acetylcholine and hemodynamic quantification of the resultant flow response in the circulatory region examined in comparison to a standard age-appropriate group (see Calver, A., Collier, J., and Vallance, P. Inhibition and stimulation of nitric oxide synthesis in the human forearm arterial bed of patients with insulin-dependent diabetes. J. Clin. Invest. 90:2548–2554, 1992; Creager, M. A., Cooke, J. P., Mendelsohn, M. E., Gallagher, S. J., Coleman, S. M., Loscalzo, J., and Dzau, V. J. Impaired vasodilation of forearm resistance vessels in hypercholesterolemic humans. J. Clin. Invest. 86:228–234, 1990; Kelm, M., Preik, M., Motz, W., and Strauer, B. E. Endotheliale Funktion bei Patienten mit arterieller Hypertonie [Endothelial function in patients with arterial hypertension]. In: Zelluläre Mechanismen der Herz-Kreislaufregulation [Cellular mechanisms of cardiovascular regulation], edited by Gante, D., Stuttgart: Schattauer, 1993, p. 139–150; Linder, L., Kiowski, W., Bühler, F. R., and Lüscher, T. F. Indirect evidence for release of endothelium-derived relaxing factor in human forearm circulation in vivo. Circulation 81:1762–1767, 1990; Panza, J. A., Epstein, S. E., and Quyyumi, A. A. Circadian variation in vascular tone and its relation to a a-sympathetic vasoconstrictor activity. N. Engl. J. Med. 325:986–990, 1991).

In addition, in longitudinal studies on this purely phenomenological approach it was sought to document a possible therapeutic effect on endothelial dysfunction in, for example, patients with arterial hypertension by hypotensive therapy with ACE inhibitors, which however, was unsuccessful because of the great variation in the methods of the investigational approach; (see Creager, M. A. and Roddy, M.-A. Effect of captopril and enalapril on endothelial function in hypertensive patients. Hypertension 24:499–505, 1994).

Moreover, the extent to which arteriosclerotically induced endothelial dysfunction is based on reduced NO synthesis and/or increased NO catabolism cannot be differentiated by the purely phenomenological approach of an altered acetylcholine-dependent flow response; (see Kelm, M., Preik, M., Köster, A., Heinzelmann, A., Motz, W., and Strauer, B. E. Reduced nitric oxide dependent vasodilation following application of organic nitrates in essential hypertension. In: The biology of nitric oxide, edited by Moncada, S., London: Portland Press Ltd., 1994, p. 509–513; Kelm, M., Feelisch M., Krebber, T., Deussen, A., Motz, W., and Strauer, B. E. The role of nitric oxide (NO) in the regulation of coronary vascular tone in hearts from hypertensive rats; maintenance of NO forming capacity and increased basal production of NO. Hypertension 25:186–193, 1995; Kelm, M., Preik, M., Hafner, D., Strauer, B. E. Evidence for a multifactorial process involved in the impaired flow responses to nitric oxide in hypertensive patients with endothelial dysfunction. Hypertension, in press, 1996).

The detection method according to the invention permits the measurement of the nitrite content in the whole blood of mammals, particularly in human whole blood, nitrite being the specific marker for the activity of endothelial constitutive NO synthesis in the human circulatory system.

The following example, Example 2, explains the detection method.

EXAMPLE 2
Method for the Determination of Nitrite in Human Whole Blood 1 ml blood is placed in a syringe containing 1 ml stop solution of 1 mol/L concentrated NaOH and immediately thereafter 50 μl of a 1 mol/L concentrated phosphoric acid ($H_3PO_4$) is added for neutralization of the blood/NaOH mixture obtained. Said mixture is centrifuged in a centrifuge (Universal 30RF, Hettich firm) for 5 min at 10,0000 g. The supernatant obtained is decanted in ultrafiltration tubes (Sartorius cut-off 10,000). It is centrifuged anew for 15 min at 2,000 g (Eppendorf centrifuge 5402 C., Eppendorf firm). The water-white ultrafiltrate obtained is transferred to reaction vessels holding 1.5 ml volumes and diluted with HPLC water in the ratio of 1:10.

This is either followed immediately by the analysis or the samples obtained are stored at −80° C. for a period of one month.

Pharmacologic Studies
1. Nitrite as Specific Diagnostic Agent of cNOS

Our own knowledge of the metabolism of NO in the human cardiovascular system was taken as the basis and, building on that, nitrite, as a specific marker of the activity of endothelial constitutive NO synthesis, was accurately and precisely measured.

The specific stop solution mentioned in Example 2 was used, which makes it possible to prevent the rapid conversion of nitrite to nitrate in human blood without thereby resulting in any appreciable loss of nitrite during sample preparation and permitting recovery of nitrite after preparation and subsequent measurement of samples. In addition, a highly sensitive method of measurement was then developed, which by means of combined ultraviolet and electrochemical detection, integrated in a 2-channel HPLC system, permits the similtaneous and highly sensitive quantification of nitrite and nitrate in samples of human whole blood or of that of mammals. The following results were obtained with test subjects:

In accordance with experimental studies, which have shown variable NO production in arterial and venous endothelial cells under basal conditions, a higher nitrite concentration (1310±50 nmol/L) was found in humans in arterial blood samples than in samples from venous vascular regions (1100±40 nmol/L). In contrast to this, as already mentioned above, serum values for nitrate exhibited no specific differences and on average amounted to 42±6 μmol/L in samples from both the arterial and venous portions of the human cardiovascular system (n=5). Additionally, it was shown by the model of the forearm circulatory system of man that local infusion of the endothelium-dependent dilators acetylcholine and bradykinin into the *A. brachialis* leads, dose-dependently, to a more than fourfold increase in flow at rest (n=7). During this increase in flow, an increase in the serum concentration of nitrite in samples from the *Vena cubitalis* was documented, dose-dependently, specifically for both mediators. Therefore, despite a more than fourfold increase in blood flow in the flow region of the forearm, a specific increase in the serum concentration of nitrite developed after infusion of the two stimulators of constitutive endothelial NO synthesis. This means that nitrite reflects, specifically and dose-dependently, increased endothelial NO production in this flow region. In addition, a highly significant correlation was found for both substances between the increase in flow and the increase in concentration of nitrite in the serum as well as the rate of release through the flow region of the forearm (see Drawings 2 and 3). Moreover, in control studies it was shown that the endothelium-independent vasodilator papaverine led to a comparable rise in blood flow by a factor of 4, without demonstrable development of an increase in the serum concentration of nitrite. Additionally, simultaneous infusion of L-NMMA as stereospecific inhibitor of constitutive endothelial NO synthesis (6 μmol/min) was shown to result in a 40% reduction in the flow response and the serum concentration of trite in comparison with control conditions (n=3). To summarize, these studies verify that, by the methodology developed, it is possible for the first time to quantify, locally and specifically, the activity of endothelial constitutive NO synthesis in the vascular system and thus to diagnose its functional state with regard to endothelial dysfunction.

2. Therapy with Authentic NO Solutions According to the Invention in the Circulatory System of Mammals, Especially in the Human Circulatory System Because of the rapid metabolism of NO in the human circulatory system, the authentic NO solutions according to the invention can be used as therapeutic agents to achieve locally very high effective concentrations of NO without triggering simultaneous deleterious systemic side effects.

Figure 4:
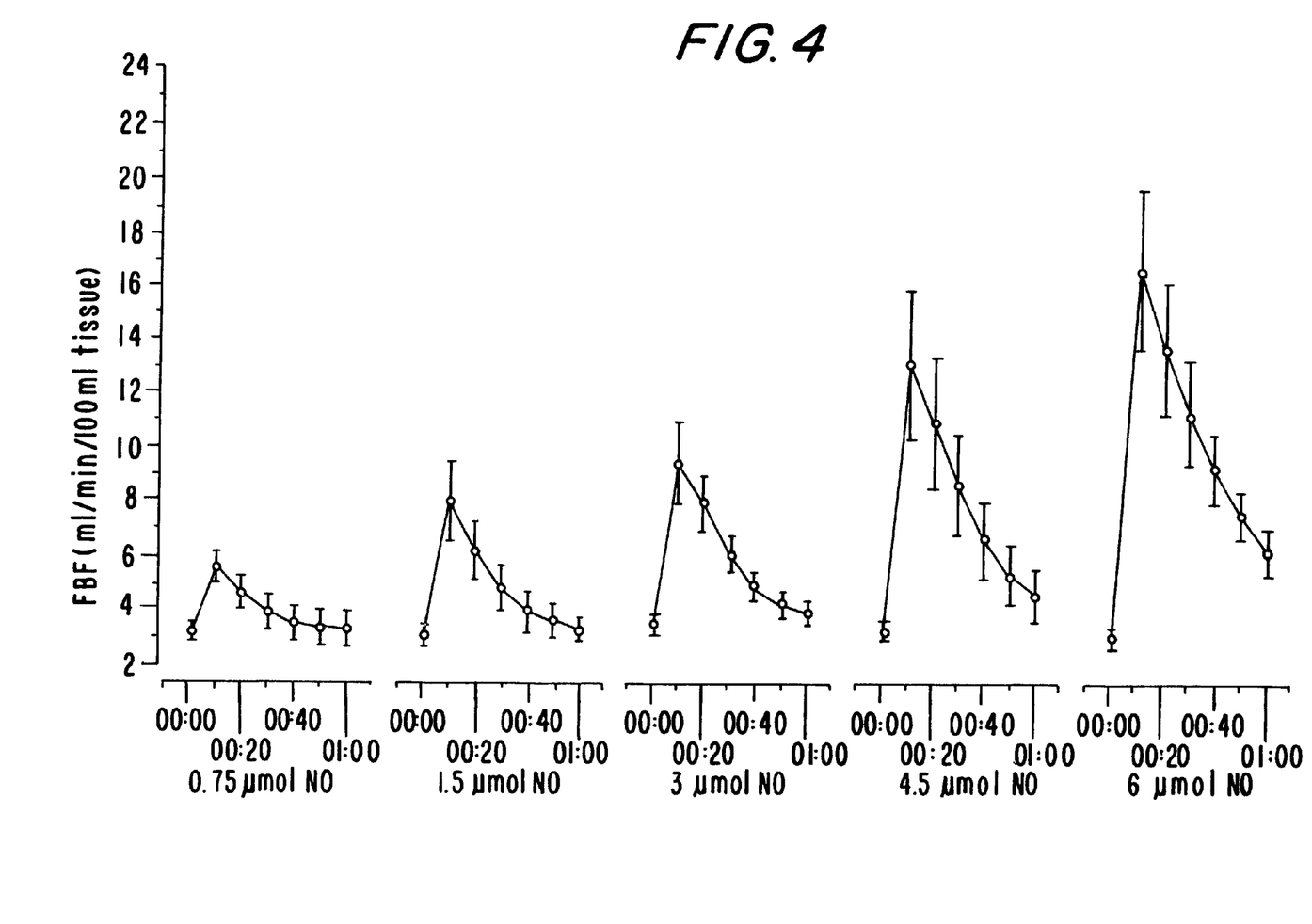
Figure 5:
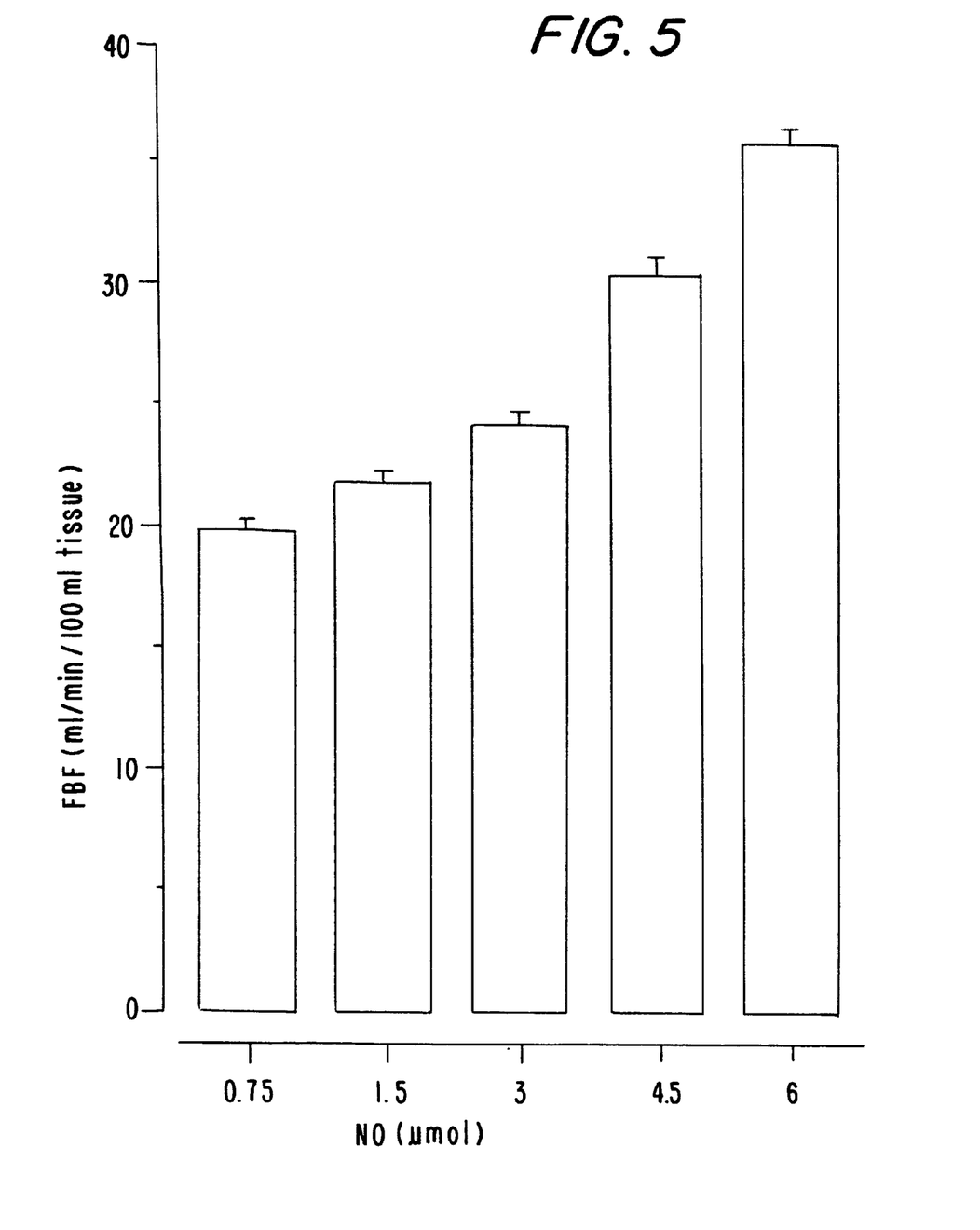
Figure 6A:
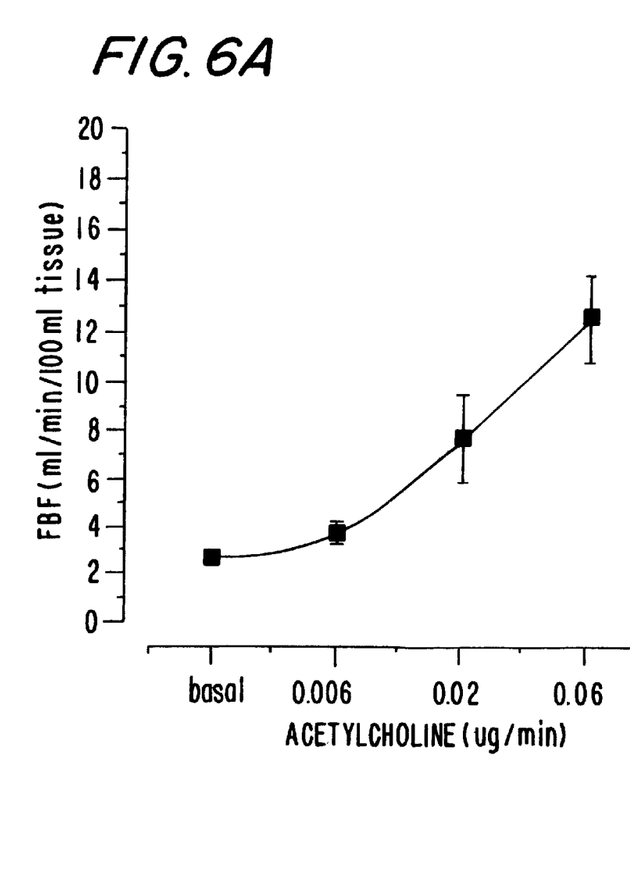
Figure 6B:
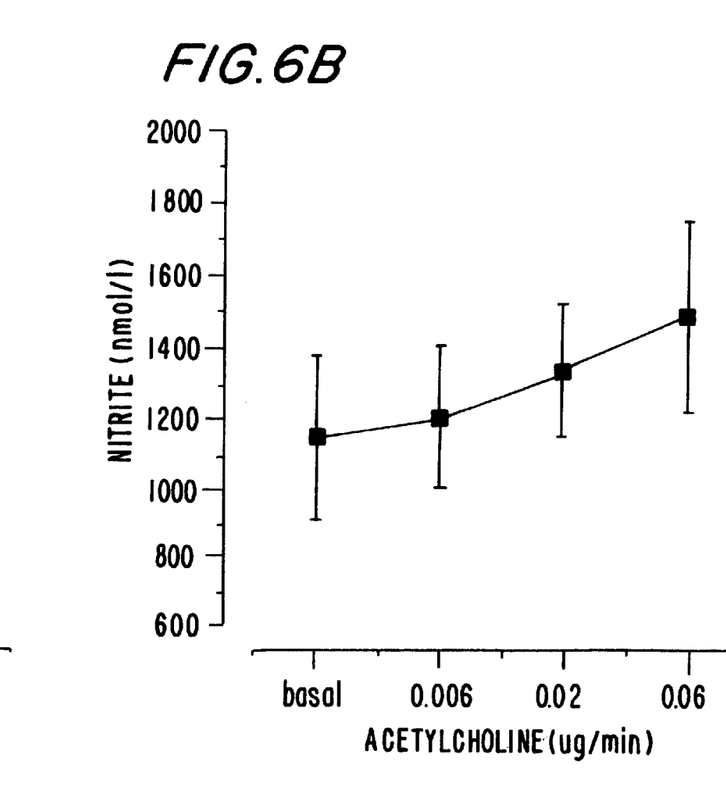
Figure 7A:
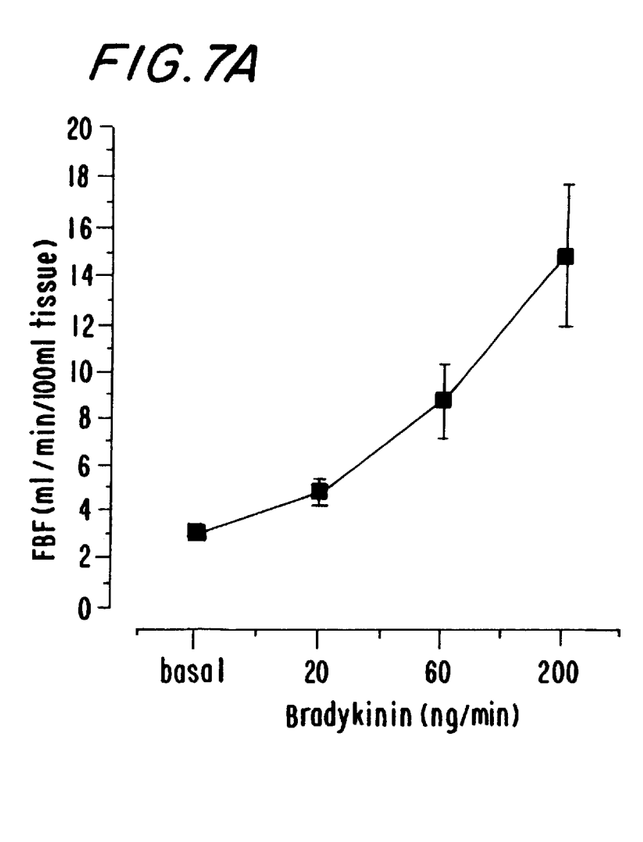
Figure 7B:
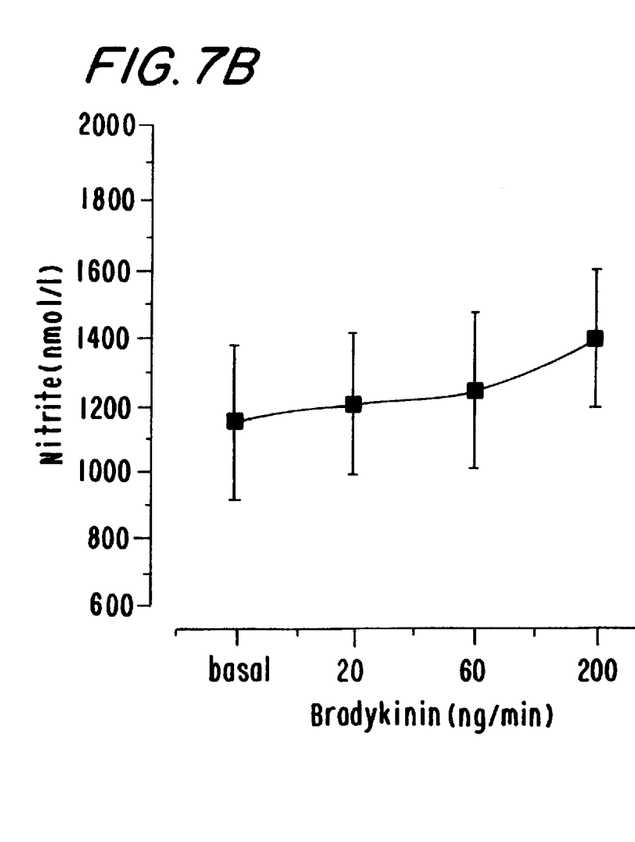

The model of forearm circulation was selected and aqueous NO standards were applied locally in increasing doses to test subjects. Because of the metabolism of NO in the human blood, a continuous infusion is not suitable for this, but the bolus technique is substantially more effective. The concentrations of the stock solution selected and the kinetics of application must be chosen so that a clearly defined bolus of the aqueous NO solution, corresponding to the circular circulatory volume and the transit time from the point of application to the resistance arteries, reproducibly reaches the targeted flow region. As can be seen in Drawings 4 and 5, by means of this bolus technique NO led reproducibly to a dose-dependent increase in blood flow at the maximum as well as over the surface under the curve of the flow response, without resulting in a systemically detectable drop in blood pressure. Further, in additional toxicologic studies it was shown that at the related doses there was no reported change in the methemoglobin content in the blood of test subjects with the application of NO during the study. Additionally, with the use of the stop solution described above, it was also shown that during NO application in this regional area of flow there was an increase in serum nitrite concentration in the *Vena cubitalis* of 111±12%, while the serum concentration for nitrate (45±8 μmol/L) did not vary significantly during the intervention. The local flow response to this aqueous NO standard applied by the bolus technique correlated highly significantly with the body surface area of the individual test subjects and was independent of the level of the heart rate or of arterial systemic blood pressure.

BRIEF DESCRIPTION OF DRAWINGS

Drawing 2

Relationship between variations in blood flow in the forearm (FBF) and serum concentration of nitrite (Drawing 2A) as well as rate of release of NO or nitrite in forearm circulation after local intra-arterial infusion of increasing doses of acetylcholine (Drawing 2B; FIG. 1). Linear regression analysis resulted in r=0.997 and P=0.003.

Drawing 3

Relationship between variations in blood flow in the forearm (FBF) and serum concentration of nitrite (Drawing 3A) as well as rate of release of NO or nitrite in forearm circulation after local intra-arterial infusion of increasing doses of bradykinin (Drawing 3B; data in FIG. 2). Linear regression analysis gave r=0.985 and P=0.001.

Drawing 4

Dose-response curve for NO-induced vasodilation in forearm circulation. The plethysmographically determined increase in blood flow in the forearm (FBF) is plotted versus the dose of NO, which was applied in bolus technique in saline standards of NO solutions (n=6, mean±SEM)

Drawing 5

Dose-response curve for NO-induced vasodilation in forearm circulation. The area under the curve is plotted for variations of FBF, same test subjects as in Drawings 4/5 (n=6, mean±SEM).

Drawings 6A, 6B, 7A and 7B show further dose-response curves of the same type as those of the previous drawings.

I claim:

1. A method for treating endothelial dysfunction in mammals, comprising intravascularly administering a therapeutically effective amount of an aqueous solution comprising nitrogen monoxide to a mammal with endothelial dysfunction.

2. A method for the adjuvant treatment of intravascular interventions in mammals comprising administering a therapeutically effective amount of an aqueous solution comprising nitrogen monoxide as an adjuvant to an intravascular intervention procedure.

3. The method of claim 2, wherein said intravascular intervention is performed on coronary arteries.

4. The method of claim 3, wherein the intravascular intervention is a percutaneous transluminal coronary angioplasty.

5. A method for the treatment of patients at increased risk for restenosis comprising intra-arterially administering to an individual at increased risk therefor a bolus dose of an effective amount of aqueous solution of NO.

6. A method of increasing blood flow in a predetermined localized area of an artery of a patient comprising
intrarterially administering a bolus dose of an aqueous solution of NO sufficient to increase blood flow in the predetermined localized area without inducing a systemically detectable drop in blood pressure.

7. A method of administering NO to a localized arterial site of a patient comprising preparing an aqueous pharmaceutical composition comprising NO by passing argon through a sterile injectable 0.9% sodium chloride solution in the absence of oxygen until any residual oxygen is removed; subsequently passing NO through the argon treated sodium chloride solution until the solution becomes saturated with NO; and intrarterially administering a bolus of the resultant NO saturated saline solution to a patient at a predetermined intrarterial site.

* * * * *